United States Patent [19]

Engel et al.

[11] Patent Number: 5,350,879
[45] Date of Patent: Sep. 27, 1994

[54] TRANSESTERIFICATION USING METAL OXIDE SOLID SOLUTIONS AS THE BASIC CATALYST

[75] Inventors: Dusan J. Engel, Barrington; Thomas P. Malloy, Lake Zurich; Peter K. Nickl, Prospect Heights, all of Ill.

[73] Assignee: UOP, Des Plaines, Ill.

[21] Appl. No.: 153,409

[22] Filed: Nov. 17, 1993

[51] Int. Cl.$^5$ .................. C07C 67/02; C07C 27/10
[52] U.S. Cl. .................................. 560/234; 568/700
[58] Field of Search .............. 560/234; 568/700, 678, 568/679, 680; 564/507

[56] References Cited

U.S. PATENT DOCUMENTS

| | | | |
|---|---|---|---|
| 5,104,987 | 4/1992 | King | 544/401 |
| 5,164,497 | 11/1992 | King et al. | 544/87 |
| 5,191,104 | 3/1993 | King | 558/260 |
| 5,191,123 | 3/1993 | King | 564/507 |
| 5,210,322 | 5/1993 | King et al. | 568/579 |

OTHER PUBLICATIONS

Nakatsuka et al., *Bull. Chem. Soc. Japan*, 52, 2449 (1979).
W. T. Reichle, *J. of Catalysis*, 94, 547 (1985).
E. Suzuki and Y. Ono, *Bull. Chem. Soc. Japan*, 61, 1008 (1988).
Nunan et al., *J. of Catalysis*, 116, 222 (1989).

*Primary Examiner*—Arthur C. Prescott
*Attorney, Agent, or Firm*—Thomas K. McBride; Eugene I. Snyder

[57] ABSTRACT

Base-catalyzed transesterification may be effected in the presence of certain metal oxide solid solutions and layered double hydroxides as the basic catalyst. Use of the latter materials as the base catalyst readily permits one to conduct transesterification in a continuous manner. Such a continuous process is applicable to esters generally and is not limited to any particular structural types of esters or alcohols. Transesterification of detergent range alkyl acetates by this method leads to the formation of the corresponding detergent range alcohols in excellent yield and with quite high selectivity.

23 Claims, No Drawings

TRANSESTERIFICATION USING METAL OXIDE SOLID SOLUTIONS AS THE BASIC CATALYST

BACKGROUND OF THE INVENTION

This application relates to transesterification. More particularly, this application relates to a continuous process of base-catalyzed transesterification. Our invention is the use of certain metal oxide solid solutions, and the layered double hydroxides from which they originate, as the basic catalyst means to effect a continuous process of transesterification.

Transesterification is a chemical reaction proceeding according to equation 1.

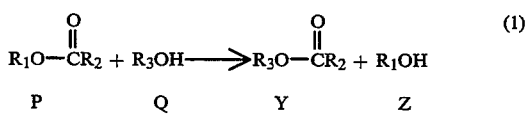

$$R_1O-\overset{O}{\overset{\|}{C}}R_2 + R_3OH \longrightarrow R_3O-\overset{O}{\overset{\|}{C}}R_2 + R_1OH \quad (1)$$

P    Q    Y    Z where P is reactant ester, Q is reactant alcohol, Y is the product ester, Z is the product alcohol and $R_1$, $R_2$ and $R_3$ are organic radicals. Transesterification may be acid catalyzed or base catalyzed. Depending upon the nature of $R_1$ and $R_3$ acid catalysis can lead to appreciable side reactions, for example, skeletal isomerization and olefin formation. Therefore base catalyzed transesterification often is favored over acid catalyzed transesterification. Where a continuous catalytic process is desired the catalyst often is used as a fixed bed. The desirability of a strong base suitable for use as a fixed bed previously has been recognized and has led to the use of materials such as, inter alia, sodium on alumina and potassium on graphite. Because of the severe limitations of such strong bases in a fixed bed, more recent attention has turned to clays and clay-like materials as suitable alternatives.

Hydrotalcite is a clay with the ideal unit cell formula of $Mg_6Al_2(OH)_{16}(CO_3.4H_2O$, and closely related analogs with variable magnesium/aluminum ratios may be readily prepared. Nakatsuka et al., *Bull. Chem. Soc. Japan,* 52, 2449 (1979) has described the catalytic use of "calcined synthetic hydrotalcite", i.e., synthesized hydrotalcite calcined at 450° C. prior to use, with varying molar ratios of $MgO/Al_2O_3$ in the batch mode polymerization of beta-propiolactone. More extensive work was reported later on the use of "synthetic hydrotalcite" in various base-catalyzed reactions by W. T. Reichle, *J. of Catalysis,* 94, 547 (1985), who found that aldol condensations in a pulse reactor were readily catalyzed by "synthetic hydrotalcite" compositions calcined at 450° C. having Mg/Al ratios from 1.3 to 6.3, although the Mg/Al ratio did not appear to have a significant effect on either its catalytic activity or efficiency. From deuterium exchange studies Reichle also concluded that the $pK_a$ of hydrotalcite was between 35 and 45. E. Suzuki and Y. Ono, *Bull. Chem. Soc. Japan,* 61, 1008 (1988), reported on the aldol condensation between formaldehyde and acetone using as catalysts two quite different types of hydrotalcite-like materials generally calcined at 500° C., both being derived from hydrotalcite itself. In one series of catalysts the carbonate moiety of hydrotalcite was exchanged by $NO_3^-$, $SO_4^{2-}$, or $CrO_4^{2-}$, and in the other series there was isomorphous substitution of $Mg^{2+}$—$Al^{3+}$ by $Li^+$—$Al^{3+}$, $Co^{2+}$—$Al^{3+}$, $Ni^{2+}$—$Al^{3+}$, or $Zn^{2+}$—$Cr^{3+}$. At 500° C. reaction temperature none of the foregoing appeared to lead to increased acetone conversion although some slight increase in selectivity (especially at lower conversion) was observed. Nunan et al., *J. of Catalysis,* 116, 222 (1989), has prepared related materials by isomorphous substitution of Mg by Cu and Zn, and of Al by Cr or Ga.

Before proceeding it appears advisable to prevent semantic obfuscation by defining several terms, using first a specific example and then generalizing by analogy. Although "hydrotalcite" is most properly applied to a clay of composition $Mg_6Al_2(OH)_{16}(CO_3).4H_2O$ often it has been used to describe related layered double hydroxides with varying Mg/Al ratios. However, after calcination of the layered double hydroxides the resulting materials are better described as solid solutions of magnesium oxide and aluminum oxide with the formula $Mg_6Al_2O_8(OH)_2$. That is, calcination destroys the layered structure characteristic of hydrotalcite and affords a solid solution. But the terminology as applied to such solid solutions often retains the "hydrotalcite" name, as in, for example, "synthetic hydrotalcites". In this application henceforth we shall try to be consistent in using the term "solid solution" of, e.g., magnesium oxide and aluminum oxide, to describe such calcined synthetic materials. The second point involves the use of the term "Mg/Al". In this application Mg/Al shall be the number ratio of magnesium to aluminum atoms in a solid solution of magnesium oxide and aluminum oxide. While this definition has been previously employed by, for example, Reichle, others have used a different definition for the Mg/Al ratio.

We can generalize the foregoing characterization to the family of layered double hydroxides having the general formula $A_aB_b(OH)_{(2a+2b)}(X^{-n})_{b/n}\cdot zH_2O$ where A is a divalent metal or combination of divalent metals, B is a trivalent metal or a combination of trivalent metals, a and b are relative number of atoms of A and B, respectively, and X is an anion, often carbonate. After calcination of the layered double hydroxide the resulting product is a solid solution of the two oxides with the formula $A_aB_bO_{(a+b)}(OH)_b$. We shall retain this distinction between layered double hydroxides and solid solutions throughout this application.

Our objective was the development of a continuous process for the transesterification of esters generally. It was important that the process be continuous and employ a fixed bed of catalyst. Therefore the catalyst had to possess suitable flow properties, compressibility, and so forth, consistent with a liquid flow. It also is important that the transesterification proceed in relatively high yield relative to thermodynamic equilibrium, with good selectivity, and at modest temperatures, say less than 300° C. Since alcohols are both a reactant product and may also be employed in large excess as a solvent, it is important that the catalysts exhibit stability in the presence of polar, hydroxylic material. We have found that solid solutions of one or more divalent metal oxides and one or more trivalent metal oxides with high surface area appear to satisfy the foregoing criteria in all respects. We also have found that their corresponding layered double hydroxides also may be utilized as a base catalyst in a continuous process of transesterification.

SUMMARY OF THE INVENTION

The purpose of this invention is to develop a continuous process for base-catalyzed transesterification using a bed of a solid base which is widely applicable as a catalyst for transesterification. An embodiment uses a broad range of metal oxide solid solutions and their corresponding layered double hydroxides as the basic catalyst. In a more specific embodiment the metal oxide solid solution is one of magnesium oxide and aluminum oxide. In a yet more specific embodiment the metal oxide solid solution is one of magnesium and aluminum oxides where the atom ratio of magnesium to aluminum is between about 1 and about 15. In still another embodiment the metal oxide solid solution is one of nickel, magnesium, and aluminum oxides. Other purposes and embodiments will be clear from the ensuing description.

DESCRIPTION OF THE INVENTION

Transesterification according to equation 1 is a kind of organic reaction which finds enormously broad applicability within organic chemistry. What we have discovered in searching for a suitable continuous process for transesterification is that a layered double hydroxide (LDH) and the metal oxide solid solution (MOSS) prepared therefrom are effective base catalysts for transesterification. The continuous process which we have developed is applicable to base-catalyzed transesterification generally and is not inherently limited to any particular class or classes of esters or alcohols. Our interest in the process is particularly high as applied to esters from detergent range alcohols, and consequently greater emphasis will be placed on this class of esters. However, it needs to be appreciated at the outset that our emphasis does not serve as a limitation on the process but merely reflects a commercial interest in a particular class of materials.

The chemical process which is the subject matter of this application is described by equation 1. In general the base catalyzed transesterification is a liquid phase reaction. Therefore, if one of the reactants is a solid there is an inference that a solvent will be used to effect homogeneity. In a particularly common variant the solvent may be one of the reactants, and typically will be the alcohol. More generally a broad range of solvents may be employed where a solvent is indicated. Since the reaction products and reactants are polar, the solvent also will usually be polar, but there are no other restrictions on the nature of the solvent that may be used in our invention other than it be unreactive under reaction conditions and be readily separable from both the reactants and products. We emphasize that the nature of the solvent neither affects nor is an important pan of our invention. Ethers, and especially polyethers, are a class of solvents which often are used in the practice of our invention, particularly the diethers of poly(ethylene glycol), such as the dimethyl ether of diethylene glycol (diglyme), the dimethyl ether of triethylene glycol (triglyme), and so forth, and ethers such as diphenyl ether. Dimethylsulfoxide and hexamethylphosphoramide are examples of two highly polar solvents which may find use in the practice of our invention.

One of the reactants P is an ester. There is no limitation on the choice of ester that may be used in the practice of our invention, for the novelty of our invention is not in the choice of either reactant, but rather in the choice of the catalyst used. In an area of particular interest to us the ester is a carboxylate of detergent range alcohols. Thus, $R_1$ is an alkyl group containing between 8 and 16 carbon atoms, and preferably between 10 and 14 carbon atoms. In a particularly preferred variant $R_1$ is a linear alkyl group, i.e., there is no branching along the paraffinic chain. The attachment of oxygen on the radical group $R_1$ is most easily explained by reference to the corresponding alcohol $R_1OH$, z. This alcohol may be either a primary or secondary alcohol, but the transesterification is particularly useful where the alcohol is a secondary alcohol although our invention is definitely not limited thereto.

The reactant ester P has therefore an alcohol portion, which contains from 8 to 16 carbon atoms and where the oxygen is so attached as to afford a primary or secondary alcohol in the product Z, and a carboxylate portion related to the carboxylic acid

As mentioned previously, our process is a general one, applicable to all classes of esters which can undergo base-catalyzed transesterification. Of particular interest as reactants are those esters where the carboxylate portion contains up to 6 carbon atoms. Thus, the carboxylates of particular interest include the formates, acetates, propionates, butyrates, valerates, and hexanoates, chloroacetates, dichloroacetates, trichloroacetates, cyanoacetates, fluoroacetates, trifluoroacetates, difluoroacetates, methoxyacetates, oxalates, malonates, succinates, glutarates, and adipates. Of these the acetates are especially preferred carboxylate groupings.

The other reactant in the base-catalyzed transesterification is the alcohol $R_3OH$, Q. The nature of Q and its amount relative to P sometimes depends upon what the purpose is of the reaction. Where the purpose of transesterification is to obtain the alcohol Z from the reactant ester P then a primary alcohol is favored as Q simply for the reason that the reaction tends to proceed most readily where $R_3OH$ is a primary alcohol. For ease of recovery of the desired product alcohol Z, that is, for the most facile separation of Z from other materials in the reaction mixture, a low boiling reactant alcohol Q is favored. Those containing from 1 to 6 carbon atoms are preferred and are exemplified by methanol, ethanol, propanol, butanol, pentanol, and the hexanols, with methanol, ethanol, butanol and propanol being most favored. Where the purpose of transesterification is to obtain Z from P it is necessary to use at least one molar proportion of Q relative to P. It is even more common to employ a large molar excess of the alcohol Q, up to 10 molar proportions and more, in order to shift the equilibrium to maximize formation of the product alcohol Z. It is not unusual to use the reactant alcohol Q in sufficient excess as to act as a solvent for the entire reaction mixture.

Where the purpose of base catalyzed transesterification is to obtain the product ester Y from P the reactant alcohol $R_3OH$ may be a primary, a secondary, or a tertiary alcohol. However, a caveat is that at high temperatures esters of tertiary alcohols may decompose to afford olefins from the tertiary alcohol portion of the ester. In this branch of our invention the relative molar ratio of P and Q depends upon whether P or Q is the more valuable material and which therefore needs to be consumed to the greatest extent. Either P or Q may be employed in excess according to the need, readily appreciated by one skilled in the art, to utilize the more valuable component as completely as possible.

The metal oxide solid solutions of this invention may be represented by the formula

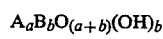

where A represents a divalent metal cation or a combination of divalent metal cations, and B represents a trivalent metal cation or some combination of trivalent metal cations. Representing the formula of our metal oxide solid solutions in this way clearly points out their basic character. The divalent metal cations used in the compositions of our invention are magnesium, nickel, zinc, calcium, barium and cobalt. Among the trivalent metal cations may be mentioned those of aluminum, chromium, gallium, and iron, in any combination, along with the trivalent lanthanides in combination with aluminum or gallium. The lanthanide metals are those of atomic number from 57 through 71 with lanthanum and cerium being the most important members of this group.

The subscripts a and b represent the relative number of atoms of the cations A and B, respectively. For the metal oxide solid solutions of our invention a/b ranges from about 1 up to about 15. That is, the relative number of atoms of the divalent metals are from about 1 up to about 15 times that of the trivalent metal, independent of the nature of A or B. The more usual range of a/b is from about 1.5 up to about 10.

The preparation of our metal oxide solid solutions stare from layered double hydroxides, which also may be employed as base catalysts for transesterification, of formula

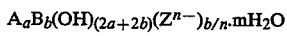

$$A_aB_b(OH)_{(2a+2b)}(Z^{n-})_{b/n} \cdot mH_2O$$

where $Z^{n-}$ is an anion, conveniently $CO_3^=$, and $mH_2O$ is water of hydration. These layered double hydroxides are prepared by mixing aqueous solutions of suitable salts of A and B, preferably at a temperature between about 0° and 10° C., to afford a precursor gel. Suitable salts of the metals in question include nitrates, carbonates, and sulfates. Other salts also may be used, especially those which decompose on calcination, such as carboxylic acid salts. (Where the layered double hydroxide is used as the base catalyst the anion $Z^{n-}$ may be a halide, nitrate, sulfate, carbonate, hydroxide, carboxylate, phosphate, and so on.) Addition is performed to a final pH of from about 9 up to about 14 and when addition is complete the mixture is stirred at a temperature generally between about 50° and about 80° C. for times which are typically on the order of 1 to about 24 hours. The layered double hydroxides which form are then collected, washed well with water, and dried, often at a temperature of about 100° C.

The metal oxide solid solutions of this invention are then prepared by calcination of the layered double hydroxide at temperatures between about 350° and about 750° C. for a time from about 1 to about 16 hours. The unusual stability of the solid solutions of a divalent metal oxide and a trivalent metal oxide prepared according to the foregoing procedure is evidenced by the fact that spinel formation is not seen until calcination temperatures of about 800° C., whereas in the prior art the spinel phase begins to appear at a calcination temperature of about 600° C. In addition, the MOSSs of our invention show greater product homogeneity as evidenced by the resistance to spinel formation.

Transesterification is effected in the presence of the metal oxide solid solutions of our invention as the base catalyst at temperatures between about 100° and about 350° C., although even higher temperatures may be employed but not necessarily with additional benefit. Transesterification is most usually performed at temperatures between about 150° and about 300° C. The pressure at which the reaction is conducted is not an important variable, that is, the pressure per se does not have a significant effect on the transesterification. However, pressures are maintained sufficiently high so as to keep the entire reaction mixture in the liquid state. Liquid hourly space velocities will depend upon such variables as temperature, the particular metal oxide solid solutions used as the catalyst, the structure of the reactant ester and reactant alcohol, and so forth. Linear hourly space velocities between about 0.1 and about 10 generally cover the useable gamut.

Base-catalyzed transesterification effected by the MOSSs and LDHs of our invention may be carried out either in a batch reaction or as a continuous process, although for commercial purposes the latter is by far preferred. In a continuous process the MOSS or LDH is used as a bed of solid catalyst, most often as a fixed bed, but also can be used as a radial bed, ebullating bed, moving bed, and so forth. Turning to the variant where a fixed bed is used, the reactants are flowed through the bed of solid catalyst at a temperature between 100° and about 350° C. at a rate affording a liquid hourly space velocity of between 0.1 and 10 reciprocal hours. Whether the reactants flow downward or upward through the bed is a matter of choice although downflow usually is preferred simply because it is more convenient.

The following examples are illustrative of our invention which is not intended to be limited thereto. Alternative embodiments, all of which are intended to be subsumed within the scope of our invention, may be readily discerned from these examples.

EXAMPLE 1

Preparation of Metal Oxide Solid Solutions: Magnesium Oxide-Aluminum Oxide Solid Solutions A 2 L, 3-necked round bottomed flask was equipped with an additional funnel, a thermometer, a mechanical stirrer, and a heating mantle. To this flask was added a solution containing 610 g of water, 60 g of $Na_2CO_3 \cdot H_2O$ and 71 g of NaOH and the contents were cooled to <5° C. The addition funnel was charged with a solution of 345 g water, 77 g $Mg(NO_3)_2 \cdot 6H_2O$ and 75 g $Al(NO_3)_3 \cdot 9H_2O$ and this solution was added over a period of 4 hours. The solution temperature was maintained at <5° C. throughout the addition and the resulting slurry was stirred for 1 hour at <5° C. The addition funnel was replaced by a reflux condenser and the slurry was heated to 60° ±5° C. for 1 hour. The slurry was then cooled to room temperature and the solids recovered by filtration. The solids were washed with 10L of hot deionized water. The solids were then dried at 100° C. for 16 hours and this product was characterized as hydrotalcite by its x-ray diffraction (XRD) pattern. After crushing, the solid was calcined at 450° C. for 12 hours in a muffle furnace with an air flow. This product was characterized as a $MgO-Al_2O_3$ solid solution (Mg/Al=1.5) by XRD. The BET surface area for this material was 285 m²/g. Materials with a different Mg/Al ratio may be prepared by similar means, changing only the relative molar ratio of $Mg(NO_3)_2 \cdot 6H_2O$ and $Al(NO_3)_3 \cdot H_2O$.

Ni/Mg/Al MOSS [Ni/Mg=3, (Ni+Mg)/Al=2].

A 2 L, 3-necked round bottomed flask was equipped with a reflux condenser, a thermometer, a mechanical stirrer, and a Glass Col heating mantle. To this 3-neck flask was added a solution containing 585 g of water, 60 g of Na2CO3.H2O and 71 g of NaOH. This flask was cooled to <5° C. An addition funnel was charged with a solution of 378 g water, 32.5 g of Mg(NO3)2 .6H2O, 110 g Ni(NO3)2.6H2O and 93 g Al(NO3)3 9H2O. The addition funnel was put in place of the reflux condenser. This solution was added over a period of 4 hours. The solution temperature was maintained at <5° C. throughout the addition. This slurry was stirred for 1 hour at <5° C. The addition funnel was removed and the reflux condenser replaced. This solution was heated to 60° C.±5° C. for 1 hour. The slurry was then cooled to room temperature and the solids recovered by filtration. The solids were washed with 10 L of hot DI water. The solids were then dried at 100° C. for 16 hours. This product was characterized as hydrotalcite by its XRD pattern. After crushing, the solid was calcined at 450° C. for 12 hours in a muffle furnace with an air flow. This product was characterized as a MgO-NiO-Al2O3 solid solution by XRD. The BET surface area for this material was 199 m$^2$/g. Alternatively, the hydrotalcite slurry/paste can be extruded prior to drying and calcining.

EXAMPLE 2

Continuous Transesterification of C12 Acetate

A mixture of C12 acetates was prepared by the addition of acetic acid to 1-dodecene and consisted primarily of 2-dodecyl acetate. The base used was 5.0 cc of 40-60 mesh of a magnesium-aluminum metal oxide solid solution at Mg/Al=2 packed into a 0.75×11.5 cm Hastelloy reactor. The feedstock was a 1:1 v/v solution of methanol:C12 acetate(molar ratio 6.5:1) passed downflow. Results are summarized in Table 1, from which it can be seen that at 270° C., 500 psig conversions of 94-95% of the acetate were achieved with a selectivity to alcohols of 98-99%.

TABLE 1

Transesterification of Dodecyl Acetates with Methanol Using a Magnesium/Aluminum MOSS (mg/Al = 2)

| TIME (hrs) | LHSV[a] | % CONV[b] | % SEL[c] |
|---|---|---|---|
| 0.0 | 1 | 94.5 | 98.9 |
| 0.6 | 1 | 94.6 | 98.8 |
| 1.1 | 1 | 94.3 | 98.8 |
| 17.5 | 0.5 | 94.4 | 98.3 |
| 18.4 | 0.5 | 94.6 | 98.1 |
| 19.2 | 0.5 | 94.4 | 98.0 |
| 25.9 | 1 | 94.7 | 98.6 |
| 41.8 | 1 | 94.6 | 98.8 |
| 45.9 | 1 | 94.4 | 98.4 |
| 49.5 | 1 | 94.2 | 98.1 |
| 65.8 | 1 | 94.2 | 97.9 |
| 69.6 | 1 | 94.3 | 98.2 |
| 73.1 | 1 | 94.2 | 97.9 |
| 90.6 | 1 | 94.3 | 98.0 |
| 95.5 | 1 | 94.2 | 98.1 |
| 97.1 | 3 | 90.7 | 98.9 |

TABLE 1-continued

Transesterification of Dodecyl Acetates with Methanol Using a Magnesium/Aluminum MOSS (mg/Al = 2)

| TIME (hrs) | LHSV[a] | % CONV[b] | % SEL[c] |
|---|---|---|---|
| 97.5 | 3 | 90.6 | 99.1 |

[a]Liquid hourly space velocity (hours$^{-1}$) based on C12 acetate only.
[b]Conversion of acetate as measured by total acetate lost.
[c]Selectivity of alcohol formed relative to acetate lost.

EXAMPLE 3

Continuous Transesterification; effect of MOSS

These experiments were conducted as described in Example 2 using the same feedstock. Results are summarized in Table 2.

TABLE 2

Continuous Transesterification of Dodecyl Acetate with Methanol

| | | | Ni/Mg/Al (Ni/Mg = 3, Ni + Mg/Al = 2) | | Mg/Al (Mg/Al = 5) % | |
|---|---|---|---|---|---|---|
| | MOSS[a] | | | | | |
| T °C. | Ppsig | LHSV[d] | % Conv.[b] | % Sel.[c] | Conv.[b] | % Sel[c] |
| 150 | 580 | 0.5 | 42.3 | 97.4 | — | — |
| 150 | 580 | 1.0 | 36.2 | 99.3 | — | — |
| 150 | 1000 | 0.5 | 25.0 | 98.4 | — | — |
| 150 | 1000 | 1.0 | 14.6 | 97.8 | — | — |
| 220 | 1000 | 0.5 | 75.9 | 98.8 | 70.9 | 55.7 |
| 220 | 1000 | 1.0 | 65.0 | 99.0 | 57.8 | 97.3 |
| 220 | 1000 | 3.0 | 46.7 | 98.7 | 43.9 | 97.4 |
| 250 | 500 | 0.5 | 91.1 | 95.0 | — | — |
| 250 | 500 | 1.0 | 88.9 | 96.6 | — | — |
| 250 | 500 | 3.0 | 74.1 | 96.4 | — | — |
| 250 | 1000 | 0.5 | 85.4 | 96.0 | 84.3 | 96.2 |
| 250 | 1000 | 1.0 | 73.6 | 96.4 | 68.7 | 93.2 |
| 250 | 1000 | 3.0 | 62.2 | 97.6 | 58.8 | 97.6 |
| 270 | 500 | 0.5 | 91.5 | 91.1 | — | — |
| 270 | 500 | 1.0 | 91.8 | 94.7 | — | — |
| 270 | 500 | 3.0 | 82.8 | 94.4 | — | — |
| 270 | 1000 | 0.5 | 92.1 | 94.9 | 94.2 | 89.1 |
| 270 | 1000 | 1.0 | 87.5 | 92.2 | 89.9 | 91.1 |
| 270 | 1000 | 3.0 | 77.7 | 96.3 | 75.1 | 95.0 |

[a]Metal oxide solid solution.
[b]Conversion of acetate (mole %) as measured by total acetate loss.
[c]Selectivity of alcohol (mole %) formed relative to acetate lost.
[d]Liquid hourly space velocity (hours$^{-1}$)based on C12 acetate only.

EXAMPLE 4

Continuous Transesterification of C13/C14 Acetates

The feedstock was a mixture of acetates dissolved in an equal volume of methanol, resulting from the addition of acetic acid to the double bonds of a stream containing 2.9% paraffins, 95.0% monoolefins, 0.6% diolefins, and 1.3% aromatics. A total of 93.5% of the stream consisted of linear, internal olefins, mostly C13 (54.1%) and C14 (39.0%) components. The acetates were composed largely of secondary alkyl acetates. A magnesium-aluminum MOSS (Mg/Al=2) (5.0 cc, 40-60 mesh) was the catalyst and feedstock was passed downflow. The results, summarized in Table 3, show not only the catalyst stability but also the combination of high conversion and high selectivity achieved when the alkyl portion of the reactant ester is a secondary alkyl group.

TABLE 3

Transesterification of Secondary Alkyl (C13/C14) Acetates[a]

| | | | PRODUCT COMPOSITION[d] | | | | | | | |
|---|---|---|---|---|---|---|---|---|---|---|
| Time | | LHSV[e] | OLEFINS | | ALCOHOLS | | ACETATES | | | |
| (Hours) | T1 °C. | Hr$^{-1}$ | C13 | C14 | C13 | C14 | C13 | C14 | % CONV[b] | % SEL[c] |
| 0 | 270 | 0.42 | 1.00 | 30.28 | 21.12 | 2.19 | 1.53 | 94.5 | 97.1 | |

TABLE 3-continued

Transesterification of Secondary Alkyl (C13/C14) Acetates[a]

| Time (Hours) | $T_1$ °C. | LHSV[e] Hr$^{-1}$ | PRODUCT COMPOSITION[d] | | | | | | % CONV[b] | % SEL[c] |
|---|---|---|---|---|---|---|---|---|---|---|
| | | | OLEFINS | | ALCOHOLS | | ACETATES | | | |
| | | | C13 | C14 | C13 | C14 | C13 | C14 | | |
| 1 | 13:49 | 1 | 0.75 | 1.53 | 11.10 | 7.74 | 1.10 | 0.77 | 93.2 | 88.5 |
| 2.1 | 14:54 | 1 | 0.73 | 1.34 | 13.59 | 9.48 | 1.78 | 1.24 | 91.0 | 91.2 |
| 8.4 | 19:12 | 0.5 | 0.67 | 0.47 | 15.01 | 10.47 | 2.74 | 1.91 | 87.4 | 95.3 |
| 9.4 | 22:12 | 0.5 | 0.57 | 0.44 | 26.84 | 18.72 | 2.27 | 1.58 | 93.6 | 97.6 |
| 12.4 | 1:12 | 0.5 | 0.61 | 0.45 | 27.85 | 19.42 | 2.58 | 1.80 | 93.0 | 97.6 |
| 15.4 | 4:12 | 0.5 | 0.60 | 0.44 | 26.21 | 18.28 | 2.81 | 1.96 | 92.0 | 97.5 |
| 18.4 | 7:11 | 0.5 | 0.60 | 0.46 | 26.69 | 18.61 | 2.58 | 1.80 | 92.7 | 97.5 |
| 19.5 | 8:17 | 0.5 | 0.84 | 1.07 | 26.10 | 18.20 | 2.29 | 1.60 | 93.5 | 95.5 |
| 20.4 | 9:09 | 0.5 | 0.98 | 1.26 | 21.80 | 15.20 | 2.05 | 1.43 | 93.2 | 93.8 |
| 26.1 | 14:51 | 1 | 0.88 | 0.52 | 21.67 | 15.11 | 2.80 | 1.95 | 90.7 | 96.0 |
| 27.0 | 15:45 | 1 | 1.62 | 1.33 | 26.45 | 18.44 | 1.99 | 1.39 | 94.5 | 93.3 |

[a]Feedstock was a 1:1 v:v acetate:methanol (molar ratio ca. 1:6.5)
[b]Percent conversion = % total acetates disappeared (mole %).
[c]Percent selectivity = % total acetates disappearing converted to alcohols (mole %).
[d]On alcohol-free basis.
[e]Liquid hourly space velocity based on acetates only.

What is claimed is:

1. A method of transesterifying a first ester with a first alcohol to form a second ester and a second alcohol as the transesterification reaction products comprising reacting the first ester with the first alcohol in the presence of a metal oxide solid solution of formula $A_aB_bO_{(a+b)}(OH)_b$ at a temperature between about 100° and 350° C. and recovering at least one of the transesterification reaction products.

2. The method of claim 1 where A is a divalent metal selected from the group consisting of magnesium, nickel, cobalt, zinc, calcium, barium, or any combination thereof, B is a trivalent metal selected from the group consisting of aluminum, chromium, gallium, iron, lanthanum, cerium, and any combination thereof, and the ratio a/b is from about 1 to about 15.

3. The method of claim 2 where A is magnesium, nickel, or a combination thereof, B is aluminum, and a/b is from about 1.5 to about 10.

4. The method of claim 1 where the first ester is an ester of an alcohol containing from about 8 up to about 16 carbon atoms.

5. The method of claim 4 where the first ester is an ester of an alcohol containing from about 10 up to about 14 carbon atoms.

6. The method of claim 1 where the first alcohol contain from 1 up to about 6 carbon atoms.

7. The method of claim 6 where the first alcohol is methanol, ethanol, butanol, or propanol.

8. The method of claim 1 where the first ester is an ester of a monocarboxylic acid of dicarboxylic acid containing up to about 6 carbon atoms.

9. The method of claim 8 where the first ester is an acetate.

10. The method of claim 1 where the first ester is an acetate of an alcohol having from 10 up to about 14 carbon atoms and the first alcohol is methanol.

11. In the transesterification of an ester with an alcohol catalyzed by a base, the improvement wherein the base is selected from the group consisting of metal oxide solid solutions of formula $A_aB_bO_{(a+b)}(OH)_b$, layered double hydroxides of formula $A_aB_b(OH)_{2a+2b}(Z^{n-})_{b/n}.mH_2O$, and all combinations thereof.

12. The improvement of claim 11 where A is a divalent metal selected from the group consisting of magnesium, nickel, cobalt, zinc, calcium, barium, or any combination thereof, B is a trivalent metal selected from the group consisting of aluminum, chromium, gallium, iron, lanthanum, cerium, and any combination thereof, and the ratio a/b is from about 1 to about 15 and $Z^{n-}$ is selected from the group consisting of halide, nitrate, carbonate, hydroxide, sulfate, carboxylate, and phosphate anions.

13. The improvement of claim 12 where A is magnesium, nickel, or a combination thereof, B is aluminum, and a/b is from about 1.5 to about 10.

14. A method of transesterifying a first ester with a first alcohol to form a second ester and a second alcohol as the transesterification reaction products comprising reacting the first ester with the first alcohol in the presence of a layered double hydroxide of formula $A_aB_b(OH)_{(2a+2b)}(Z^{n-})_{b/n}.mH_2O$ at a temperature between about 100° and 350° C. and recovering at least one of the transesterification reaction products.

15. The method of claim 14 where A is a divalent metal selected from the group consisting of magnesium, nickel, cobalt, zinc, calcium, barium, or any combination thereof, B is a trivalent metal selected from the group consisting of aluminum, chromium, gallium, iron, lanthanum, cerium, and any combination thereof, and the ratio a/b is from about 1 to about 15, and $Z^{n-}$ is selected from the group consisting of halide, nitrate, carbonate, hydroxide, sulfate, carboxylate, and phosphate anions.

16. The method of claim 15 where A is magnesium, nickel, or a combination thereof, B is aluminum, and a/b is from about 1.5 to about 10.

17. The method of claim 14 where the first ester is an ester of an alcohol containing from about 8 up to about 16 carbon atoms.

18. The method of claim 17 where the first ester is an ester of an alcohol containing from about 10 up to about 14 carbon atoms.

19. The method of claim 14 where the first alcohol contain from 1 up to about 6 carbon atoms.

20. The method of claim 19 where the first alcohol is methanol, ethanol, butanol or propanol.

21. The method of claim 14 where the first ester is an ester of a monocarboxylic acid or dicarboxylic acid containing up to about 6 carbon atoms.

22. The method of claim 21 where the first ester is an acetate.

23. The method of claim 14 where the first ester is an acetate of an alcohol having from 10 up to about 14 carbon atoms and the first alcohol is methanol.

* * * * *